United States Patent [19]

Chiba et al.

[11] Patent Number: 4,985,425

[45] Date of Patent: Jan. 15, 1991

[54] DISSOLVED COMPOSITION OF [BENZO-1,2,4-THIADIAZINE]-1,1-DIOXIDE

[75] Inventors: Tadahiro Chiba; Kiyoshi Miyazawa; Makoto Uzuka; Takashi Suzuki, all of Yokohama, Japan

[73] Assignee: Shiseido Company Ltd., Tokyo, Japan

[21] Appl. No.: 146,451

[22] Filed: Jan. 21, 1988

Related U.S. Application Data

[63] Continuation-in-part of Ser. No. 89,386, Aug. 25, 1987, abandoned.

[30] Foreign Application Priority Data

Jan. 22, 1987 [JP] Japan ............................ 62-013061
Feb. 5, 1987 [JP] Japan ............................ 62-025439
Feb. 23, 1987 [JP] Japan ............................ 62-039757

[51] Int. Cl.$^5$ .................... A61K 7/06; A61K 9/08; A61K 31/395
[52] U.S. Cl. .................... 514/222.2; 424/47; 514/222.5; 514/222.8; 514/880; 514/881; 514/938
[58] Field of Search ............ 544/12; 514/222.2, 222.5, 514/222.8, 880, 881

[56] References Cited

U.S. PATENT DOCUMENTS

| | | | |
|---|---|---|---|
| 3,210,346 | 10/1965 | Werner et al. ............... | 544/12 |
| 3,527,864 | 9/1970 | Kilmer Mac Millan et al. .... | 424/70 |
| 4,022,894 | 5/1977 | Fainberg et al. ............. | 514/272 |
| 4,184,039 | 1/1980 | Soldati et al. .............. | 544/12 |
| 4,329,335 | 5/1982 | Su et al. ................... | 424/70 |
| 4,740,519 | 4/1988 | Shroot et al. ............... | 514/443 |

FOREIGN PATENT DOCUMENTS

| | | | |
|---|---|---|---|
| 0027655 | 4/1981 | European Pat. Off. ............. | 424/70 |
| 02222670 | 5/1987 | European Pat. Off. ............. | 424/70 |
| 56-65811 | 6/1981 | Japan . | |
| 63-93708 | 4/1988 | Japan . | |

OTHER PUBLICATIONS

The Journal of Pediatrics, vol. 71, No. 4, 494–505 (1967), Baker.
Conn's, Current Therapy, 1984, pp. 599–603.
Conn, Current Therapy, 1981, p. 662.

Primary Examiner—Dale R. Ore
Attorney, Agent, or Firm—Sprung, Horn, Kramer & Woods

[57] ABSTRACT

A dissolved composition containing (A) one or more of [benzo-1,2,4-thiadiazine]-1,1-dioxide derivatives, (B) dimethyl sulfoxide, benzyl alcohol, or the mixture thereof; (C) water; and (D) one or more anionic surfactants and/or surfactants, other than anionic surfactants, having a nitrogen atom in the molecule thereof, or (D') n-decylmethyl sulfoxide, or (D") (i) one or more ampholytic surfactants and/or nonioni-cationic-polar surfactants and (ii) one or more nonionic surfactants having a nitrogen atom in the molecule thereof and, optionally, (E) isopropyl alcohol and (F) a pH controller.

This dissolved composition is effective as an ingredient for a hair germination and hair growth promoting agent.

26 Claims, No Drawings

DISSOLVED COMPOSITION OF [BENZO-1,2,4-THIADIAZINE]-1,1-DIOXIDE

CROSSREFERENCE TO RELATED APPLICATION

This application is a continuation-in-part of Ser. No. 89,386, filed Aug. 25, 1987, now abandoned.

BACKGROUND OF THE INVENTION

1. Field of the Invention

The present invention relates to a [benzo-1,2,4-thiadiazine]-1,1-dioxide dissolved composition and a hair germination and hair growth promoting agent containing the same as an effective ingredient. More specifically, it relates to a dissolved composition comprising (A) one or more of [benzo-1,2,4-thiadiazine]-1,1-dioxide derivatives (hereinafter called "the dioxide"); (B) dimethyl sulfoxide (hereinafter called "DMSO"); and/or benzyl alcohol (hereinafter called "BA"); (C) water; and (D) one or more anionic surfactants and/or one or more surfactants, other than anionic surfactants, having a nitrogen atom in the molecule thereof, or (D') n-decylmethyl sulfoxide (hereinafter called "n-DeMeSO"), or (D") (i) one or more ampholytic surfactants and/or nonionic-cationic-polar surfactants and (ii) one or more nonionic surfactants, having a nitrogen atom in the molecule thereof.

Furthermore, the present invention concerns a hair germination, hair growth promoting agent containing the dissolved composition as an effective ingredient. This dissolved composition can be utilized in the field of pharmaceuticals or the field of cosmetics.

2. Description of the Related Art

Dioxide has been used in the prior art as a therapeutical agent for hypertension, by injection, and as a therapeutical agent for hypoglycemia due to excessive secretion of insulin, by oral administration, but the generation of hypertrichosis has been reported as a side effect thereof (see: The Journal of Pediatrics, Vol. 71, No. 4, pp. 494–505, 1967).

On the basis of the above, an invention using dioxide as the hair germination, hair growth promoting agent by external application was disclosed in Japanese Unexamined Patent Publication (Kokai) No. 56-65811 and in Japanese Patent Application No. 60-256167.

In these inventions, as a main solvent for the dioxide, DMSO is used in the former and BA is used in the latter. However, the hair germination and hair growth promoting effects thereof are not satisfactory and, therefore, there is still a demand for hair treatment agents having greater hair germination and hair growth promoting effects.

SUMMARY OF THE INVENTION

Accordingly, the objects of the present invention are to eliminate the above-mentioned disadvantages of the prior art and to provide a dissolved composition comprising dioxide having greater hair germination and hair growth promoting effects.

Another object of the present invention is to provide a hair germination and hair growth promoting agent, which has greater hair germination and hair growth promoting effects, and further has a high skin safety factor, an excellent useability, and a high stability.

Other objects and advantages of the present invention will be apparent from the following description.

In accordance with the present invention, there is provided a dissolved composition comprising (A) at least one [benzo-1,2,4-thiadiazine]-1,1-dioxide derivative (i.e., "the dioxide"); (B) dimethyl sulfoxide (i.e., "DMSO"), benzyl alcohol (i.e., "BA"), or the mixture thereof; (C) water; and (D) at least one surfactant selected from the group consisting of anionic surfactants and surfactants, other than anionic surfactants, having a nitrogen atom in the molecule thereof, or (D') n-decylmethyl sulfoxide (i.e., "n-DeMeSO"), or (D") (i) at least one surfactant selected from the group consisting of ampholytic surfactants and (ii) at least one surfactant selected from the group consisting of nonionic surfactants having a nitrogen atom in the molecule thereof.

This dissolved composition according to the present invention, especially, has greater hair germination and hair growth promoting effects and, therefore, is useful in the fields of pharmaceuticals and cosmetics.

Thus, in accordance with the present invention, there is also provided a hair germination and hair growth promoting agent containing, as an effective ingredient, the above-mentioned dissolved composition.

DESCRIPTION OF THE PREFERRED EMBODIMENTS

The dioxide to be used as the component (A) in the present invention is a substance known as a therapeutical agent for hypertension and as a therapeutical agent for hypoglycemia based on an excessive secretion of insulin, and is a compound represented by the formula shown below

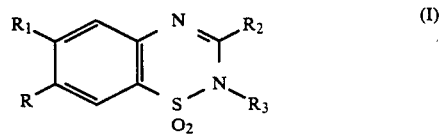

wherein R is Cl, CF$_3$, SO$_2$, or NH$_2$, R$_1$ is H, Cl, SO$_2$, or NH$_2$, R$_2$ is H, C$_n$H$_{2n+1}$ wherein n is an integer of 1 to 10, CH$_2$OH, COOH, or CH$_2$C$_6$H$_5$, and R$_3$ is H, C$_m$H$_{2m+1}$ wherein m is an integer of 1 to 10, or CH$_2$C$_6$H$_5$.

An amount of about 0.005% to 10% by weight of the dioxide may be formulated in the dissolved composition of the present invention. When used as a hair germination or the hair growth promoting agent, the hair germination or the hair growth promoting effect becomes greater as the formulated amount is increased, but in view of the occurrence of side effects when a large amount is used, it should be less than 10%. Preferably, an amount of 0.01% to 7% by weight is used.

The amount of DMSO used as the component (B) in the present invention may be 1.0% to 30% by weight, preferably 2.0% to 10% by weight. The amount of BA also used as the component (B) in the present invention may be 1.0% to 30% by weight, preferably 3.0% to 15% by weight. These DMSO and BA may be used alone or in a mixture thereof as a solvent.

The amount of water used as the component (C) in the present invention may be 1.0% to 70% by weight, preferably 3.0% to 50% by weight.

The formulation amounts of these solvents (i.e., DMSO, BA, and water) may be appropriately determined depending upon the amount of the dioxide formulated or the combination of the solvents.

The anionic surfactants usable as the component (D) in the first aspect of the present invention (i.e., "surfactant (D-1)") may include those having one or more of a carboxyl groups, sulfonyl groups, sulfonic acid ester (i.e., sulfate) groups, and phosphoric acid ester (i.e., phosphate) groups in the molecule thereof. Examples of the surfactants having a carboxyl group are fatty acid soaps, ether carboxylic acids and their salts, and carboxylic acid salts of, for example, condensation products of amino acids and fatty acids. Examples of the surfactants having a sulfonyl group are alkylsulfonates, sulfosuccinic acid, ester sulfonates, alkylaryl and alkyl naphthalene sulfonates, N-acylsulfonates, and formaldehyde condensation sulfonates. Example of the surfactants having a sulfate group are sulfated oils, ester sulfates, alkyl sulfates, ether sulfates, alkylaryl ether sulfates, and amide sulfates. Examples of the surfactants having a phosphate group are alkyl phosphates, amide phosphates, ether phosphates, and alkylaryl ether phosphates. These surfactants may be used alone or in any mixture thereof.

The surfactants, other than the anionic surfactant, having a nitrogen atom in the molecule thereof and usable also as the component (D) in the present invention (i.e., "surfactant (D-2)") may include ampholytic surfactants, nonionic-cationic surfactants, nonionic surfactants and cationic surfactants having a nitrogen atom in the molecule thereof. Examples of the ampholytic surfactants are carboxybetaines, sulfobetaines, amino carboxylates, and imidazoline derivatives. Examples of the nonionic-cationic surfactants are amine oxides. Examples of the nonionic surfactants are fatty acid alkanol amides, polyoxyethylene fatty acid amides, esters of alkanol amines, and polyoxyethylene alkylamines. Examples of the cationic surfactants are fatty acid amine salts, alkyl quaternary ammonium salts, aromatic quaternary ammonium salts, pyridinium salts, and imidazolinium salts. These surfactants may be used alone or in any mixture thereof.

The above-mentioned surfactants (D-1) and (D-2) may be used alone or as a combination thereof. Preferably, the surfactants (D-1) and (D-2) are used in combination at a molar ratio of 20:1 to 1:20, more preferably 10:1 to 1:10. The total amount of the component (D) used in the present invention is preferably 0.001% to 10% by weight, more preferably 0.01% to 5% by weight, when the surfactants (D-1) and (D-2) are used alone or in combination. When the amount of the component (D) is less than 0.001% by weight, the desired increase in the hair germination and hair growth promoting effect is not sufficiently realized. Conversely, when the amount of the component (D) is more than 10% by weight, the skin safety factor is lowered.

The amount of n-DeMeSO used as the component (D') in the second aspect of the present invention is 0.1% to 10% by weight, preferably 0.5% to 7.0% by weight, based on the weight of the total composition. When the amount of the n-DeMeSO is less than 0.1% by weight, the desired hair germination and hair growth promoting effects are not sufficiently realized. Conversely, when the amount of the component (D') is more than 10% by weight, the skin safety factor tends to be lowered.

The surfactant component (D") in the third aspect of the present invention includes (i) one or more ampholytic surfactants (i.e., "surfactant (D"-1)") and/or one or more nonionic-cationic-polar surfactants (i.e., "surfactant (D"-2)") and (ii) one or more nonionic surfactants having a nitrogen atom in the molecule thereof (i.e., "surfactant (D"-3)").

Examples of ampholytic surfactants (D"-1) usable in the present invention are carboxybetaines such as N,N-dimethyl-N-lauryl-N-carboxymethyl ammonium betaine and N,N-dimethyl-N-oleyl-N-carboxymethyl ammonium betaine; imidazoline derivatives such as 2-lauryl-N-carboxyethyl-N-hydroxyethyl imidazolium betaine and 2-lauryl-N-carboxymethyl-N-hydroxyethyl imidazolium betaine; aminocarboxylic acid salts such as sodium N-coconutalkyl-$\beta$-aminodipropionate and disodium N-coconutalkyl-$\beta$-aminodipropionate; sulfobetaines; and aminobetaines.

Examples of the nonionic-cationic-polar surfactants (D"-2) usable in the present invention amine oxides such as lauryl dimethyl amine oxide and bis-(2-hydroxyethyl) laurylamine oxide.

In the third aspect of the present invention, one or more surfactants selected from the above-mentioned ampholytic surfactants (D"-1) and the above-mentioned semi-polar surfactants (D"-2) are used.

Examples of the nonionic surfactants having a nitrogen atom in the molecule thereof, i.e., surfactant (D"-3), are fatty acid alkanol amides, polyoxyethylene fatty acid amides, esters of alkanol amines, and polyoxyethylene alkyl amines.

In the third aspect of the present invention, one or more surfactants (D"-1) and/or (D"-2) and one or more surfactants (D"-3) are used as a mixture. Preferably, (i) the surfactants (D"-1) and/or (D"-2) to (ii) the surfactants (D"-3) are mixed in a molar ratio (i)/(ii) of 20/1 to 1/40, more preferably 10/1 to 1/20. The total amount of the surfactants (D"-1) and/or (D"-2) and the surfactants (D"-3) is preferably 0.001% to 10% by weight, more preferably 0.01% to 5% by weight. When the total amount of the component (D") is less than 0.001% by weight, the desired increase in the hair germination and hair growth promoting effect is not sufficiently realized. Conversely, when the total amount of the component (D") is more than 10% by weight, the skin safety factor tends to be lowered.

Furthermore, the dissolved composition according to the present invention may optionally include (E) isopropyl alcohol(i.e., hereinafter "IPA") to enhance the skin safety factor, in addition to the above-mentioned solvents. The amount of IPA when formulated is preferably 10% to 85% by weight, more preferably 20% to 60% by weight, although there are no critical limitations to the addition amount of IPA as long as the effects of the present invention are not adversely affected.

Furthermore, according to the present invention, (F) a pH controller may be optionally formulated into the dissolved composition to adjust the pH to 8.5 to 11.0, to increase the solubility of the dioxide.

As the pH controller in the above-mentioned system, either an inorganic salt or an organic salt or a buffer may be used, provided that the pH is controlled to 8.5 to 11.0, preferably 9.5 to 11.0. If the pH is lower than 8.5, the solubility of the dioxide is sometimes unsatisfactory. On the other hand, a pH of over 11.0 is not desirable from the safety aspect.

The dissolved composition or the hair germination and hair growth promoting agent according to the present invention can be further formulated by, in addition to the dioxide, sterilizers such as salicylic acid, resorcin and hexachlorophen; vitamins such as nicotinic acid, vitamin E, vitamin A acid, pantothenic acid, ethynyl estradiol, hinokitiol, glycyrrhetic acid, biotin and others; and chemicals such as fatty acids, amino acids, etc., which are generally used in hair germination, hair promoting agents. Also, if desired, and if within the scope which will not impair the effect of the present invention, it is possible to formulate various components generally employed for pharmaceuticals or cosmetics; for example, aqueous components, powder components, oil components, surfactants other than those mentioned above, humectants, thickeners, preservatives, antioxidants, perfumes, colorants.

The dissolved composition of the present invention contains a dioxide having an high skin safety factor, excellent useability, and a good stability over a long-term period, and further, a transparent gel-like dissolved composition can be obtained by the addition of a thickener, and a liquid emulsion, cream, aerosol, and other conventional forms of preparations can be also obtained.

EXAMPLES

The present invention will now be further illustrated by, but is by no means limited to, the following Examples, wherein "%" is on a weight basis unless otherwise specified.

Test Method

The hair germination effects of the compositions obtained in Examples 1, 16, and 28 and Comparative Examples 1 and 2, 3 and 4, and 5 to 7, respectively, were evaluated by using C3H/HeNCrJ mice at the resting phase of the hair cycle according to an Ogawa et al method set forth in "Normal and Abnormal Epidermal Differentiation" p 159–170, 1982, edited by M. Seiji and I.A. Bernstein, published by Tokyo University Printing Dept. That is, the mice were divided into a Control group (i.e., no application), an Example group, and Comparative groups each consisting of ten mice. The hair on the back of the mice was removed by an electric hair clipper and shaver, and 0.1 ml of each sample was applied to the shaved back once a day.

The effect of hair germination or growth was evaluated by comparing the area ratio after measuring the hair growth on the shaved portion of the back of the mouse.

Example 1: Transparent Liquid Composition

| (1) | 7-Chloro-3-methyl-2H- [benzo-1,2,4-thiadiazine]-1,1-dioxide | 3.0% |
|---|---|---|
| (2) | BA | 15.0 |
| (3) | IPA | 42.0 |
| (4) | Sodium dodecyl sulfate | 0.08 |
| (5) | Dodecyl dimethyl amine oxide | 0.16 |
| (6) | Sodium hydroxide | q.s. |
| (7) | Purified water | balance |

Preparation method

After dissolving (6) in (7), (1) was added thereto, followed by heating to a temperature of 50° C. while stirring, thus dispersing (1). Then, (2), (3), (4), and (5) were successively added thereto while stirring, and thus a transparent liquid composition having a pH of about 10.2 was obtained.

Comparative Example 1

| (1) | 7-Chloro-3-methyl-2H-[benzo-1,2,4-thiadiazine]-1,1-dioxide | 3.0% |
|---|---|---|
| (2) | BA | 15.0 |
| (3) | IPA | 42.0 |
| (4) | Sodium hydroxide | q.s. |
| (5) | Purified water | balance |

Preparation method

This composition was prepared in a manner similar to Example 1. The pH of the resultant composition was about 10.2.

Comparative Example 2

| (1) | BA | 15.0% |
|---|---|---|
| (2) | IPA | 42.0 |
| (3) | Sodium hydroxide | q.s. |
| (4) | Potassium dihydrogen phosphate | q.s. |
| (5) | Purified water | balance |

Preparation method (1) and (2) were added to (5) and, after mixing the mixture with stirring, appropriate amounts of (3) and (4) were added. The pH was controlled to about 10.2.

Evaluation Results

The compositions prepared in Example 1 and Comparative Examples 1 and 2 were evaluated according to the above-mentioned test method. In all groups, no growth of hair was observed until 8 days after the application of the sample compositions. At 9 days after the application, the backs of the mice belonging to Example 1 group became darker and the hair at the Anagen phase was observed. On the other hand, in about half of the mice belonging to Comparative Example 1 group, the hair at the Anagen phase was observed 14 days after the application. At 20 days after the application, only some mice in the Control group and Comparative Example 2 groups were observed to have Anagen phase. The days at which a 50% hair growth was observed are shown in each sample composition in Table 1.

TABLE 1

| Sample | 50% Hair growth (day) | Promoting days (days) |
|---|---|---|
| Control | 31 | — |
| Example 1 | 12 | 19 |
| Comparative Ex. 1 | 21 | 10 |
| Comparative Ex. 2 | 31 | 0 |

As is clear from the results shown in Table 1, the sample composition of Example 1 exhibited a remarkable hair growth and growth promoting effects when compared to Comparative Examples 1 and 2.

Example 2: Transparent Liquid Composition

| (1) | 7-Chloro-3-methyl-2H-[benzo-1,2,4-thiadiazine]-1,1-dioxide | 3.0% |
|---|---|---|
| (2) | BA | 15.0 |
| (3) | IPA | 42.0 |
| (4) | Sodium dodecyl sulfate | 0.08 |
| (5) | Sodium hydroxide | q.s. |
| (6) | Purified water | balance |

Preparation method

A transparent liquid composition was prepared according to the method of Example 1. The pH of the composition was about 10.2.

Example 3: Transparent Liquid Composition

| (1) | 7-Chloro-3-methyl-2H-[benzo-1,2,4-thiadiazine]-1,1-dioxide | 3.0% |
|---|---|---|
| (2) | BA | 15.0 |
| (3) | IPA | 42.0 |
| (4) | Dodecyl dimethyl amine oxide | 0.16 |
| (5) | Sodium hydroxide | q.s. |
| (6) | Purified water | balance |

A transparent liquid composition was prepared according to the method of Example 1. The pH of the composition was about 10.2.

Example 4: Transparent Liquid Composition

| (1) | 7-Chloro-3-methyl-2H-[benzo-1,2,4-thiadiazine]-1,1-dioxide | 3.0% |
|---|---|---|
| (2) | BA | 10.0 |
| (3) | IPA | 50.0 |
| (4) | Dipropylene glycol | 5.0 |
| (5) | Sodium laurate | 0.07 |
| (6) | N,N-dimethyl-N-lauryl-N-carboxymethyl ammonium betaine | 0.2 |
| (7) | Sodium hydroxide | q.s. |
| (8) | Purified water | balance |

Preparation method

After (7) was dissolved in (8), (1) was added thereto, followed by heating to 50° C. to thoroughly disperse (1) in the mixture. Thereafter, (2), (3), (4), (5), and (6) were added and the mixture mixed together while stirring. Thus, (1) was dissolved to obtain a transparent liquid composition. The pH of the composition was about 10.2.

Effect

The transparent liquid composition of Example 4 was applied to ten healthy men aged 25 to 50 having male alopecia and depilation symptoms, at a dose of 2 to 4 ml once or twice per day for 3 months.

The results are shown in Table 2.

TABLE 2

| Subject | Age | Growth | Depilation |
|---|---|---|---|
| A | 35 | Effective | Effective |
| B | 47 | Not effective | " |
| C | 32 | Effective | " |
| D | 50 | Not effective | " |
| E | 29 | Effective | " |
| F | 35 | " | " |
| G | 38 | " | " |
| H | 25 | " | " |
| I | 36 | " | " |
| J | 33 | " | " |

As is clear from the results shown in Table 2, the transparent liquid composition of Example 4 was effective against depilation in all of the subjects and had a high efficiency of 80% for promoting growth.

Example 5: Transparent Liquid Composition

| (1) | 7-Chloro-3-methyl-2H-[benzo-1,2,4-thiadiazine]-1,1-dioxide | 10.0% |
|---|---|---|
| (2) | BA | 20.0 |
| (3) | IPA | 50.0 |
| (4) | Sodium dodecyl sulfate | 0.06 |
| (5) | Dodecyl dimethyl amine oxide | 0.2 |
| (6) | Sodium hydroxide | q.s. |
| (7) | Purified water | balance |

A transparent liquid composition was prepared in the same manner as in Example 4. The pH of the composition was about 10.7.

Example 6: Transparent Liquid Composition

| (1) | 7-Chloro-3-methyl-2H-[benzo-1,2,4-thiadiazine]-1,1-dioxide | 6.0% |
|---|---|---|
| (2) | BA | 15.0 |
| (3) | IPA | 45.0 |
| (4) | Dipropylene glycol | 4.0 |
| (5) | Polyoxyethylene (3 mole) lauryl ether sulfate | 1.4 |
| (6) | N,N-dimethyl-N-lauryl-N-carboxymethyl ammonium betaine | 1.7 |
| (7) | Sodium hydroxide | q.s. |
| (8) | Sodium citrate | q.s. |
| (9) | Purified water | balance |

Preparation method (7) and (8) were dissolved in (9) and, thereafter, a transparent liquid composition was prepared according to the method of Example 4. The pH of the composition was about 10.5.

Example 7: Transparent Liquid Composition

| (1) | 7-Chloro-3-methyl-2H-[benzo-1,2,4-thiadiazine]-1,1-dioxide | 1.0% |
|---|---|---|
| (2) | BA | 7.0 |
| (3) | DMSO | 5.0 |
| (4) | IPA | 50.0 |
| (5) | Polyethylene glycol 200 | 5.0 |
| (6) | Sodium dodecyl sulfate | 0.6 |
| (7) | Sodium dodecyl phosphate | 0.6 |
| (8) | Sodium lauryl isothiocyanate | 0.3 |
| (9) | Lauryl dimethyl amine oxide | 1.15 |
| (10) | Potassium hydroxide | q.s. |
| (11) | Purified water | balance |

Preparation method

A transparent liquid composition was prepared according to the method of Example 4. The pH of the composition was about 9.3.

Example 8: Transparent Liquid Composition

| (1) | 7-Chloro-3-methyl-2H-[benzo-1,2,4-thiadiazine]-1,1-dioxide | 5.0% |
|---|---|---|
| (2) | BA | 15.0 |
| (3) | IPA | 50.0 |
| (4) | Aqueous sodium lactate soln. (50%) | 8.0 |
| (5) | Sodium laurate | 0.2 |
| (6) | Sodium-N-dodecyl glutamate | 0.7 |
| (7) | Sodium-N-dodecyl sarcosinate | 0.56 |
| (8) | 2-Dodecyl-1-hydroxyethyl-1-carboxymethyl imidazolinium betaine | 0.7 |
| (9) | Lauric diethanolamide | 0.9 |
| (10) | Sodium hydroxide | q.s. |
| (11) | Purified water | balance |

Preparation method

A transparent liquid composition was prepared according to the method of Example 4. The pH of the composition was about 10.6.

Example 9: Transparent Liquid Composition

| | | |
|---|---|---|
| (1) | 7-Chloro-3-methyl-2H-[benzo-1,2,4-thiadiazine]-1,1-dioxide | 4.0% |
| (2) | DMSO | 10.0 |
| (3) | IPA | 45.0 |
| (4) | Sodium dodecylphosphate | 1.1 |
| (5) | 2-Dodecyl-1-hydroxyethyl-1-carboxymethyl imidazolinium betaine | 1.7 |
| (6) | Sodium hydroxide | q.s. |
| (7) | Purified water | balance |

Preparation method

A transparent liquid composition was prepared according to Example 4. The pH of the composition was about 10.4.

Example 10: Hair Tonic

| | | |
|---|---|---|
| (1) | 7-Chloro-3-methyl-2H-[benzo-1,2,4-thiadiazine]-1,1-dioxide | 0.03% |
| (2) | Hinokitiol | 0.01 |
| (3) | Retinol palmitate | 0.1 |
| (4) | Vitamin E acetate | 0.05 |
| (5) | Vitamin $B_6$ | 0.1 |
| (6) | BA | 10.0 |
| (7) | IPA | 25.0 |
| (8) | Ethyl alcohol | 35.0 |
| (9) | Propylene glycol | 5.0 |
| (10) | Perfume | q.s. |
| (11) | Sodium laurate | 0.45 |
| (12) | Lauric diethanolamide | 0.20 |
| (13) | Polyoxyethylene (15 mole) oleyl alcohol | 4.0 |
| (14) | Sodium hydroxide | q.s. |
| (15) | Purified water | balance |

Preparation method

After (14) was dissolved in (15), (1) was added thereto; followed by heating to 50° C. (6), (7), (9), (11), and (12) were then added, while stirring to dissolve (1) in the mixture. Thus, a transparent liquid composition (A) was prepared.

On the other hand, (2), (3), (4), (5), (10), and (13) were successively added and dissolved in (8), and thus the composition (B) was prepared. The composition (B) was added to the composition (A), while stirring. The mixture was then stirred and mixed, followed by filtration, and thus a transparent liquid hair tonic was prepared.

Example 11: Gel Type Hair Growth Preparation

| | | |
|---|---|---|
| (1) | 7-Chloro-3-methyl-2H-[benzo-1,2,4-thiadiazine]-1,1-dioxide | 2.0% |
| (2) | Hirokitiol | 0.01 |
| (3) | Pantothenyl ethyl ether | 0.05 |
| (4) | BA | 10.0 |
| (5) | IPA | 40.0 |
| (6) | Dipropylene glycol | 10.0 |
| (7) | Glycerol | 5.0 |
| (8) | Hydroxypropyl cellulose | 1.0 |
| (9) | Carboxyvinyl polymer | 1.0 |
| (10) | Sodium dodecyl sulfate | 0.03 |
| (11) | Lauric diethanol amide | 2.75 |
| (12) | Polyoxyethylene hydrogenated castor oil (P.O.E. = 60 mole) | 2.0 |
| (13) | Sodium hydroxide | q.s. |
| (14) | Purified water | balance |

Preparation method

After (13) was dissolved in a portion of (14), (1) was added thereto, followed by heating to 50°) C., and thus (1) was thoroughly dispersed. To this mixture, (6), (7), a portion of (5), (4), (10), and (11) were successively added, followed by stirring, and thus (1) was completely dissolved to obtain the transparent liquid composition (A).

On the other hand, (2), (3), and (12) were dissolved in the remainder of (5), followed by dispersing (8) therein. Thus, the composition (B) was prepared.

Furthermore, (9) was dispersed and dissolved in the remainder of (14) to prepare the composition (C).

While stirring, the composition (C) was added to the composition (B), followed by thoroughly mixing. The composition (A) was gradually added to this mixture, and thus a transparent gel-like composition was obtained.

Example 12: Gel-like Hair Growth Preparation

| | | |
|---|---|---|
| (1) | 7-Chloro-3-methyl-2H-[benzo-1,2,4-thiadiazine]-1,1-dioxide | 0.02% |
| (2) | Ethynyl estradiol | 0.002 |
| (3) | Vitamin E acetate | 0.05 |
| (4) | BA | 5.0 |
| (5) | IPA | 20.0 |
| (6) | Ethyl alcohol | 25.0 |
| (7) | 1,3-Butadiene glycol | 5.0 |
| (8) | Diethylene glycol | 5.0 |
| (9) | Glycerol | 4.0 |
| (10) | Sodium α-olefin sulfonate | 0.8 |
| (11) | Dodecyl dimethyl amine oxide | 1.6 |
| (12) | Hydroxypropyl cellulose | 1.2 |
| (13) | Carboxyvinyl polymer | 0.8 |
| (14) | Diisopropanol amine | 0.3 |
| (15) | Potassium hydroxide | q.s. |
| (16) | Purified water | balance |

Purification method

A gel-like hair growth preparation was prepared according to the method of Example 10, except that the transparent liquid composition (A) was prepared from (1), (4), (5), (7), (8), (9), (10), (11), (14), (15) and a portion of (16), the composition (B) was prepared from (2), (3), (6), and (12), and the composition (C) was prepared from (13) and the remainder of (16).

Example 13: Emulsion

| | | |
|---|---|---|
| (1) | 7-Chloro-3-methyl-2H-[benzo-1,2,4-thiadiazine]-1,1-dioxide | 0.05% |
| (2) | BA | 5.0 |
| (3) | IPA | 20.0 |
| (4) | Dipropylene glycol | 15.0 |
| (5) | Liquid paraffin | 3.0 |
| (6) | Cetyl alcohol | 0.2 |
| (7) | Sodium dodecyl sulfate | 1.73 |
| (8) | Dodecyl dimethyl amine oxide | 0.92 |
| (9) | Carboxyvinyl polymer | 0.2 |
| (10) | Perfume | q.s. |
| (11) | Polyoxyethylene hydrogenated castor oil (P.O.E. = 40 mol) | 1.0 |
| (12) | Preservative | q.s. |
| (13) | Sodium hexamethaphosphate | 0.03 |
| (14) | Potassium hydroxide | q.s. |

-continued

| Example 13: Emulsion | |
|---|---|
| (15) Purified water | balance |

Preparation method

After (14) was dissolved in a portion of (15), (1) was added thereto, followed by heating to 50° C., and thereafter, a portion of (4), (3), and (2) were added thereto, whereby (1) was dissolved. Furthermore, (7) and (8) were added and the mixture was dissolved to prepare the composition (A).

To the remainder of (4), a portion of (15) and (11) were added and the mixture was dissolved upon heating to 50° C. While the mixture was stirred in a homomixer, the mixture obtained by adding (6), (10), and (12) to (5), followed by mixing at 70° C was gradually added, and thus the emulsified composition (B) was obtained.

After (9) and (13) were dissolved in the remainder of (15), the compositions (B) and (A) obtained above were successively added thereto while stirring, followed by mixing under stirring in a homomixer. After cooling, an emulsion was obtained.

Example 14: Cream

| Example 14: Cream | |
|---|---|
| (1) 7-Chloro-3-methyl-2H-[benzo-1,2,4-thiadiazine]-1,1-dioxide | 0.1% |
| (2) Vitamin E acetate | 0.05 |
| (3) BA | 5.0 |
| (4) IPA | 25.0 |
| (5) Polyethylene glycol 200 | 13.0 |
| (6) Glycerol | 4.0 |
| (7) Liquid paraffin | 1.0 |
| (8) Castor oil | 3.5 |
| (9) Perfume | q.s. |
| (10) Sodium dodecyl sulfate | 2.0 |
| (11) N,N-dimethyl-N-lauryl-N-carboxymethyl ammonium betaine | 0.9 |
| (12) Glycerol monofatty acid ester | 1.5 |
| (13) Preservative | q.s. |
| (14) Clay mineral (bentonite) | 6.0 |
| (15) Potassium hydroxide | q.s. |
| (16) Purified water | balance |

Preparation method

After (15) was added and dissolved in a portion of (16), (1) was added and the mixture was heated to 50° C. Then, (3), (4), (5), (6) were added to dissolve (1), and (10) and (11) were then added, followed by dissolving while stirring. Thus, the composition (A) was prepared.

To (7) were successively added (2), (8), (9), (12), and (13), the mixture heated to 70° C., and mixed to prepare a solution, and thus the composition (B) was prepared.

At a temperature maintained at 70° C, while stirring the composition (A), the composition (B) was gradually added to effect preliminary emulssification, followed by emulsification by a homomixer.

This emulsion was added to a dispersion previously prepared by adding (14) to the remainder of (16) under stirring, and the mixture then cooled to obtain a cream.

Example 15: Aerosol

| Example 15: Aerosol | |
|---|---|
| Stock solution recipe | |
| (1) 7-Chloro-3-methyl-2H-[benzo-1,2,4-thiadiazine]-1,1-dioxide | 0.6% |
| (2) Ethynyl estradiol | 0.001 |
| (3) Pantothenyl ethyl ether | 0.05 |
| (4) BA | 6.0 |
| (5) IPA | 37.0 |
| (6) Ethyl alcohol | 37.0 |
| (7) Dipropylene glycol | 15.0 |
| (8) Sodium laurate | 1.0 |
| (9) Polyoxyethylene hydrogenated castor oil (P.O.E.: 60 mole) | 1.0 |
| (10) Perfume | q.s. |
| (11) Sodium hydroxide | q.s. |
| (12) Purified water | balance |
| Filling recipe | |
| (13) Stock solution | 30.0% |
| (14) Freon 12 | 42.0 |
| (15) Freon 13 | 28.0 |

Preparation method

A stock solution was prepared according to the method of Example 10.

Filling was carried out by filling the stock solution (13) at a prescribed amount into a can and, after mounting a valve, the gases (14) and (15) were successively filled in prescribed amounts.

Example 16: Transparent Liquid Composition

| Example 16: Transparent Liquid Composition | |
|---|---|
| (1) 7-Chloro-3-methyl-2H-[benzo-1,2,4-thiadiazine]-1,1-dioxide | 3.0% |
| (2) BA | 13.0 |
| (3) IPA | 44.0 |
| (4) n-DeMeSO | 7.0 |
| (5) Sodium hydroxide | q.s. |
| (6) Purified water | balance |

Preparation method

After (5) was added and dissolved in (6), (1) was added, followed by heating to 50° C., and thus (1) was dispersed therein while stirring. Then, (2), (3), and (4) were successively added, followed by mixing while stirring to obtain a transparent liquid composition. The pH of the composition was about 10.2.

Comparative Example 3:

| Comparative Example 3: | |
|---|---|
| (1) 7-Chloro-3-methyl-2H-[benzo-1,2,4-thiadiazine]-1,1-dioxide | 3.0% |
| (2) BA | 13.0 |
| (3) IPA | 44.0 |
| (4) Sodium hydroxide | q.s. |
| (5) Purified water | balance |

Preparation method

The transparent liquid composition was prepared according to the method of Example 16. The pH was about 10.2.

Comparative Example 4

| Comparative Example 4 | |
|---|---|
| (1) BA | 13.0% |

-continued

| Comparative Example 4 | |
|---|---|
| (2) IPA | 44.0 |
| (3) Sodium hydroxide | q.s. |
| (4) Potassium dihydrogen phosphate | q.s. |
| (5) Purified water | balance |

Preparation method (1) and (2) were added to (5), followed by mixing while stirring. Then, appropriate amounts of (3) and (4) were added thereto to prepare a composition having a pH of about 10.2.

Evaluation Results

The compositions prepared in Example 16 and Comparative Examples 3 and 4 were evaluated according to the above-mentioned test method.

In all groups, no hair growth was observed until 9 days after the application of the sample compositions. At 10 days after the application, the backs of the mice belonging to the Example 16 group became darker and the hair at the Anagen phase was observed. On the other hand, about half of the mice belonging to the Comparative Example 3 group were transferred to the Anagen hair at 14 days after the application, and some mice belonging to the Control group and Comparative Example 4 group were transferred to the Anagen hair at 20 days after the application. The rates of hair growth at 25 days after the application are shown in Table 3.

TABLE 3

| Sample | Rate of Hair Growth 25 days after application (%) |
|---|---|
| Control | 40 |
| Example 16 | 90 |
| Comparative Ex. 3 | 65 |
| Comparative Ex. 4 | 40 |

As is clear from the results shown in Table 3, the sample composition of Example 16 exhibited a remarkable hair growth effect when compared to Comparative Examples 3 to 4.

Example 17: Transparent Liquid Composition

| Example 17: Transparent Liquid Composition | |
|---|---|
| (1) 7-Chloro-3-methyl-2H-[benzo-1,2,4-thiadiazine]-1,1-dioxide | 3.0% |
| (2) BA | 10.0 |
| (3) IPA | 50.0 |
| (4) Dipropylene glycol | 5.0 |
| (5) n-DeMeSO | 5.0 |
| (6) Sodium hydroxide | q.s. |
| (7) Purified water | balance |

Preparation method

After (6) was added and dissolved in (7), (1) was added, followed by heating to 50° C., and thus (1) was thoroughly dispersed therein. Then, (2), (3), (4), and (5) were add ed, followed by mixing while stirring, and (1) and (5) were dissolved therein to prepare a transparent liquid composition. The pH of the composition was about 10.2.

Effect

The transparent liquid composition of Example 1 7 was applied to the healthy men aged 27 to 49 having male alopecia and depilation symptoms, at a dose of 2 to 4 ml once or twice a day for 3 months.

The results are shown in Table 4.

TABLE 4

| Subject | Age | Hair growth | Depilation |
|---|---|---|---|
| A | 29 | Effective | Effective |
| B | 39 | Not effective | " |
| C | 34 | Effective | " |
| D | 27 | " | " |
| E | 46 | Not effective | " |
| F | 30 | Effective | " |
| G | 33 | " | " |
| H | 41 | " | " |
| I | 49 | Not effective | " |
| J | 32 | Effective | " |

As is clear from the results shown in Table 4, the transparent liquid composition of Example 17 was effective against depilation in all the subjects and had a high efficiency of 70% for promoting hair growth.

Example 18: Transparent Liquid Composition

| Example 18: Transparent Liquid Composition | |
|---|---|
| (1) 7-Chloro-3-methyl-2H-[benzo-1,2,4-thiadiazine]-1,1-dioxide | 1.0% |
| (2) BA | 7.0 |
| (3) DMSO | 5.0 |
| (4) IPA | 50.0 |
| (5) Polyethylene glycol 400 | 4.0 |
| (6) n-DeMeSO | 6.0 |
| (7) Potassium hydroxide | q.s. |
| (8) Purified water | balance |

Preparation method

A transparent liquid composition was prepared according to the method of Example 17. The pH of the composition was about 9.3.

Example 19: Transparent Liquid Composition

| Example 19: Transparent Liquid Composition | |
|---|---|
| (1) 7-Chloro-3-methyl-2H-[benzo-1,2,4-thiadiazine]-1,1-dioxide | 10.0% |
| (2) BA | 20.0 |
| (3) IPA | 50.0 |
| (4) n-DeMeSO | 1.0 |
| (5) Sodium hydroxide | q.s. |
| (6) Purified water | balance |

Preparation method

A transparent liquid composition was prepared according to the method of Example 17. The pH of the composition was about 10.7.

Example 20: Transparent Liquid Composition

| Example 20: Transparent Liquid Composition | |
|---|---|
| (1) 7-Chloro-3-methyl-2H-[benzo-1,2,4-thiadiazine]-1,1-dioxide | 6.0% |
| (2) BA | 15.0 |
| (3) IPA | 45.0 |
| (4) Dipropylene glycol | 4.0 |
| (5) Aqueous sodium lactate solution (50%) | 6.0 |
| (6) n-DeMeSO | 1.0 |
| (7) Sodium hydroxide | q.s. |
| (8) Sodium citrate | q.s. |

15

-continued

| Example 20: Transparent Liquid Composition | |
|---|---|
| (9) Purified water | balance |

Preparation method (7) and (8) were added and dissolved in (9) and, thereafter, a transparent liquid composition was prepared according to the method of Example 17. The pH of the composition was about 10.5.

Example 21: Transparent Liquid Composition

| Example 21: Transparent Liquid Composition | |
|---|---|
| (1) 7-Chloro-3-methyl-2H-[benzo-1,2,4-thiadiazine]-1,1-dioxide | 4.0% |
| (2) DMSO | 10.0 |
| (3) IPA | 45.0 |
| (4) Polyethylene glycol 200 | 5.0 |
| (5) n-DeMeSO | 3.0 |
| (6) Sodium hydroxide | q.s. |
| (7) Purified water | balance |

Preparation method

A transparent liquid composition was prepared according to the method of Example 17. The pH of the composition was about 10.4.

Example 22: Hair Tonic

| Example 22: Hair Tonic | |
|---|---|
| (1) 7-Chloro-3-methyl-2H-[benzo-1,2,4-thiadiazine]-1,1-dioxide | 0.02% |
| (2) Hinokitiol | 0.01 |
| (3) Retinol palmitate | 0.1 |
| (4) Vitamin E acetate | 0.05 |
| (5) Vitamin $B_6$ | 0.1 |
| (6) BA | 10.0 |
| (7) IPA | 25.0 |
| (8) Ethyl alcohol | 35.0 |
| (9) Propylene glycol | 5.0 |
| (10) Perfume | q.s. |
| (11) Polyoxyethylene (15 mole) oleyl alcohol | 4.0 |
| (12) n-DeMeSO | 0.5 |
| (13) Potassium hydroxide | q.s. |
| (14) Purified water | balance |

Preparation method

After (13) was added and dissolved in (14), (1) was added thereto, followed by heating to 50° C. (6), (7), (9), and (12) were then added, followed by mixing while stirring. Thus, (1) and (12) were dissolved to prepare a transparent liquid composition (A).

On the other hand, (2), (3), (4), (5), (10), and (11) were successively added to (8), followed by stirring, and thus the dissolved composition (B) was obtained.

While stirring the composition (A), the composition (B) was gradually added thereto, followed by mixing and filtering, and thus a transparent liquid hair tonic was prepared.

Example 23: Gel-like Hair Growth Preparation

| Example 23: Gel-like Hair Growth Preparation | |
|---|---|
| (1) 7-Chloro-3-methyl-2H-[benzo-1,2,4-thiadiazine]-1,1-dioxide | 2.0% |
| (2) Hinokitiol | 0.01 |
| (3) Pantothenyl ethyl ether | 0.05 |
| (4) BA | 10.0 |
| (5) IPA | 40.0 |
| (6) Dipropylene glycol | 10.0 |
| (7) Glycerol | 5.0 |
| (8) Hydroxypropyl cellulose | 1.0 |
| (9) Carboxyvinyl polymer | 1.0 |
| (10) Polyoxyethylene (60 mole) hydrogenated castor oil | 2.0 |
| (11) n-DeMeSO | 2.0 |
| (12) Sodium hydroxide | q.s. |
| (13) Purified water | balance |

Preparation method

After (12) was added and dissolved in a portion of (13), (1) was added thereto, the mixture heated to 50° C., and (1) was well dispersed while stirring. To the dispersion (6), (7), a portion of (5), (4), and (11) were successively added, while stirring, to dissolve (1) and (11) therein. Thus, the transparent liquid composition (A) was prepared.

On the other hand, (2), (3), and (10) were dissolved in the remainder of (5) and (8) was dispersed therein to prepare the composition (B).

Furthermore, (9) was dispersed and dissolved in the remainder of (13) to prepare the composition (C).

While stirring the composition (B), the composition (C) was added thereto and the mixture was thoroughly mixed. Furthermore, to this mixture, the composition (A) was gradually added, followed by mixing while stirring. Thus, a transparent gel-like composition was prepared.

Example 24: Gel-like Hair Growth Preparation

| Example 24: Gel-like Hair Growth Preparation | |
|---|---|
| (1) 7-Chloro-3-methyl-2H-[benzo-1,2,4-thiadiazine]-1,1-dioxide | 0.03% |
| (2) Ethynyl estradiol | 0.002 |
| (3) Vitamin E acetate | 0.05 |
| (4) BA | 5.0 |
| (5) IPA | 20.0 |
| (6) Ethyl alcohol | 25.0 |
| (7) 1,3-Butadiene glycol | 5.0 |
| (8) Diethylene glycol | 5.0 |
| (9) Glycerol | 4.0 |
| (10) Hydroxypropyl cellulose | 1.2 |
| (11) Carboxyvinyl polymer | 0.8 |
| (12) n-DeMeSO | 0.3 |
| (13) Diisopropanol amine | 0.3 |
| (14) Sodium hydroxide | q.s. |
| (15) Purified water | balance |

Preparation method

A gel-like hair growth preparation was prepared according to the method of Example 23, except that the transparent liquid composition (A) was prepared from (1), (4), (5), (7), (8), (9), (12), (13), (14), and a portion of (15) and the composition (B) was prepared from (2), (3), (6), and (10), and the composition (C) was prepared from (11) and the remainder of (15).

Example 25: Emulsion

| | |
|---|---|
| (1) 7-Chloro-3-methyl-2H-[benzo-1,2,4-thiadiazin]-1,1-dioxide | 0.1% |
| (2) BA | 5.0 |

-continued

| | | |
|---|---|---|
| (3) IPA | 20.0 | |
| (4) Dipropylene glycol | 15.0 | |
| (5) Liquid paraffin | 3.0 | |
| (6) Cetyl alcohol | 0.2 | |
| (7) Carboxyvinyl polymer | 0.2 | |
| (8) Perfume | q.s. | |
| (9) n-DeMeSO | 0.7 | |
| (10) Polyoxyethylene hydrogenated castor oil (P.O.E. = 40 mole) | 1.0 | |
| (11) Preservative | q.s. | |
| (12) Sodium hexamethaphosphate | 0.03 | |
| (13) Potassium hydroxide | q.s. | |
| (14) Purified water | balance | |

Preparation method

After (13) was added and dissolved in a portion of (14), (1) was added thereto, followed by heating to 50° C. Then, a portion of (4), (3), and (2) were added to dissolve (1) therein. Furthermore, (9) was added and dissolved while mixing, and thus the composition (A) was prepared.

To the remainder of (4) were added and dissolved a portion of (14) and (10) while heating at 50° C. While the solution was stirred by a homomixer, a mixture prepared by adding (6), (8), and (11) to (5) under heating at 70° C. was gradually added to be emulsified therein, and thus composition (B) was prepared.

After (7) and (12) were added and dissolved in the remainder of (14), while stirring the solution, composition (B) and composition (A) were successively added thereto. Further, the mixture was mixed while stirring by a mixer and then cooled to obtain an emulsion.

Example 26 Cream:

| | | |
|---|---|---|
| (1) 7-Chloro-3-methyl-2H-[benzo-1,2,4-thiadiazine]-1,1-dioxide | 0.06% | |
| (2) Vitamin E acetate | 0.05 | |
| (3) BA | 5.0 | |
| (4) IPA | 25.0 | |
| (5) Polyethylene glycol 200 | 13.0 | |
| (6) Glycerol | 4.0 | |
| (7) Liquid paraffin | 1.0 | |
| (8) Castor oil | 3.5 | |
| (9) Perfume | q.s. | |
| (10) Glycerol monofatty acid ester | 1.5 | |
| (11) n-DeMeSO | 1.0 | |
| (12) Preservative | q.s. | |
| (13) Clay mineral (bentonite) | 6.0 | |
| (14) Potassium hydroxide | q.s. | |
| (15) Purified water | balance | |

Preparation method

After (14) was added and dissolved in a portion of (15), (1) was added and the mixture heated to 50° C. Then, (3), (4), (5), and (11) were added to dissolve (1) and (11). Thus the composition (A) was prepared.

To (7) were successively added (2), (8), (9), (10), and (12), the mixture was heated to 70° C. and mixed to prepare a solution, and thus the composition (B) was prepared.

At a temperature maintained at 70° C., composition (B) was gradually added to composition (A), while stirring to effect preliminary emulsification, followed by emulsification by a homomixer.

This emulsion was added to a dispersion previously prepared by adding (13) to the remainder of (15) while stirring, and the mixture then cooled to prepare a cream.

Example 27 Aerosol

| Stock solution recipe | | |
|---|---|---|
| (1) 7-Chloro-3-methyl-2H-[benzo-1,2,4-thiadiazine]-1,1-dioxide | 0.6% | |
| (2) Ethynyl estradiol | 0.001 | |
| (3) Pantothenyl ethyl ether | 0.05 | |
| (4) BA | 6.0 | |
| (5) IPA | 37.0 | |
| (6) Ethyl alcohol | 37.0 | |
| (7) Dipropylene glycol | 15.0 | |
| (8) Polyoxyethylene hydrogenated castor oil (POE = 60 mole) | 1.0 | |
| (9) n-DeMeSO | 2.5 | |
| (10) Perfume | q.s. | |
| (11) Sodium hydroxide | q.s. | |
| (12) Purified water | balance | |
| Filling recipe | | |
| (13) Stock solution | 30.0% | |
| (14) Freon 12 | 42.0 | |
| (15) Freon 13 | 28.0 | |

Preparation method

A stock solution was prepared in the same way as in Example 22.

Filling was carried out by filling the stock solution (13) at a prescribed amount into a can and, after mounting a valve, the gases (14) and (15) were successively filled in prescribed amounts.

Example 28: Transparent Liquid Composition

| | | |
|---|---|---|
| (1) 7-Chloro-3-methyl-2H-[benzo-1,2,4-thiadiazine]-1,1-dioxide | 3.0% | |
| (2) DMSO | 10.0 | |
| (3) IPA | 45.0 | |
| (4) N,N-dimethyl-N-lauryl-N-carboxy-ammonium betaine | 2.6 | |
| (5) lauric diethanol amide | 0.31 | |
| (6) Sodium hydroxide | q.s. | |
| (7) Purified water | balance | |

Preparation method

After adding (1), (2), and (3) to (7), the mixture was agitated and dispersed, followed by adding (4) and (5) thereto. Then, (6) was added thereto so that a pH of the solution became 10.2. The mixture was thoroughly stirred to obtain the desired clear liquid solution.

Comparative Example 5

| | | |
|---|---|---|
| (1) 7-Chloro-3-methyl-2H-]benzo-1,2,4-thiadiazine]-1,1-dioxide | 3.0% | |
| (2) DMSO | 10.0 | |
| (3) IPA | 45.0 | |
| (4) Sodium hydroxide | q.s. | |
| (5) Purified water | balance | |

Preparation Method

This composition was prepared in a manner similar to Example 28.

Comparative Example 6

| | | |
|---|---|---|
| (1) 7-Chloro-3-methyl-2H-[benzo-1,2,4- | 3.0% | |

-continued

| | | |
|---|---|---|
| thiadiazine]-1,1-dioxide | | |
| (2) DMSO | 10.0% | |
| (3) IPA | 45.0 | |
| (4) Polyoxyethylene hydrogenated castor oil (P.O.E. = 60 mole) | 2.0 | |
| (5) Sodium hydroxide | q.s. | |
| (6) Purified water | balance | |

Preparation method

This composition was prepared in a manner similar to Example 28.

Comparative Example 7

| Comparative Example 7 | |
|---|---|
| (1) DMSO | 10.0% |
| (2) IPA | 45.0 |
| (3) Sodium hydroxide | q.s. |
| (4) Potassium dihydrogen phosphate | q.s. |

Preparation method (1) and (2) were added to (5) and, after mixing the mixture with stirring, appropriate amounts of (3) and (4) were added. The pH was controlled to about 10.2.

Evaluation Results

The compositions prepared in Example 28 and Comparative Examples 5 to 7 were evaluated according to the above-mentioned test method. In all groups, no growth of hair was observed until 9 days after the application of the sample compositions. At 10 days after the application, the backs of the mice belonging to the Example 28 group became darker and the hair at the Anagen phase was observed. On the other hand, in about half of the mice belonging to the Comparative Examples 5 and 6 groups, the hair of the Anagen phase was observed 14 days after the application. At 20 days after the application, only some mice in the Control group and Comparative Example 7 group were observed to have hair at the Anagen phase. The days at which a 90% hair growth was observed are shown in each sample composition in Table 5.

TABLE 5

| Sample | 90% Hair growth (day) | Promoting days (days) |
|---|---|---|
| Control | 43 | — |
| Example 28 | 25 | 18 |
| Comparative Ex. 5 | 34 | 9 |
| Comparative Ex. 6 | 32 | 11 |
| Comparative Ex. 7 | 43 | 0 |

As is clear from the results shown in Table 5, the sample composition of Example 2888 exhibited remarkable hair growth and growth promoting effects when compared to Comparative Examples 5 to 7.

Example 29: Transparent Liquid Composition

| | | |
|---|---|---|
| (1) 7-Chloro-3-methyl-2H[benzo-1,2,4-thiadiazin]-1,1-dioxide | 3.0% | |
| (2) BA | 10.0 | |
| (3) IPA | 50.0 | |
| (4) Dipropylene glycol | 5.0 | |
| (5) 2-Lauryl-1-hydroxyethyl-1-carboxymethyl imidazolium betaine | 0.04 | |
| (6) Polyoxyethylene (10 mole) oleyl amine | 0.63 | |
| (7) Sodium hydroxide | q.s. | |
| (8) Purified water | balance | |

Preparation method (1), (2), (3), (4), (5), and (6) were added to (8), followed by heating at 50° C. to disperse (1) in the mixture. After cooling, (7) was added to adjust the pH of the solution to about 10.2 The mixture was stirred to dissolve (1) therein, and thus a clear liquid composition was obtained.

Effect

The transparent liquid composition of Example 29 was applied to ten healthy men aged 26 to 46 having male alopecia and depilation symptoms, at a dose of 2 to 4 ml once or twice per day for 3 months The results are shown in Table 6.

TABLE 6

| Subject | Age | Growth | Depilation |
|---|---|---|---|
| A | 26 | Effective | Effective |
| B | 37 | " | " |
| C | 31 | " | " |
| D | 42 | Not effective | " |
| E | 45 | Effective | " |
| F | 36 | " | " |
| G | 29 | " | " |
| H | 38 | Not effective | " |
| I | 33 | Effective | " |
| J | 46 | Not effective | " |

As is clear from the results shown in Table 6, the transparent liquid composition of Example 29 was effective against depilation in all of the subjects and had a high efficiency of 70% for promoting hair growth.

Example 30: Transparent Liquid Composition

| | | |
|---|---|---|
| (1) 7-Chloro-3-methyl-2H-[benzo-1,2,4-thiadiazine]-1,1-dioxide | 10.0% | |
| (2) BA | 20.0 | |
| (3) IPA | 50.0 | |
| (4) 2-Lauryl-1-hydroxyethyl-1-carboxymethyl imidazolium betaine | 1.2 | |
| (5) N,N-Dimethyl-N-lauryl-N-carboxy ammonium betaine | 1.0 | |
| (6) Lauric diethanolamide | 0.9 | |
| (7) Sodium hydroxide | q.s. | |
| (8) Purified water | balance | |

Preparation method

A transparent liquid composition was prepared in the same manner as in Example 29. The pH of the composition was about 10.7.

Example 31: Transparent Liquid Composition

| | | |
|---|---|---|
| (1) 7-Chloro-3-methyl-2H-[benzo-1,2,4-thiadiazine]-1,1-dioxide | 6.0% | |
| (2) BA | 15.0 | |
| (3) IPA | 45.0 | |
| (4) Dipropylene glycol | 4.0 | |
| (5) N,N-dimethyl-N-lauryl-N-carboxymethyl ammonium betaine | 2.0 | |
| (6) Lauryl dimethylamine oxide | 0.9 | |
| (7) Lauric diethanol amide | 0.6 | |
| (8) Sodium hydroxide | q.s. | |
| (9) Trisodium citrate | q.s. | |

Preparation method

A transparent liquid composition was prepared according to the method of Example 29. The pH of the composition was adjusted to about 10.5.

Example 32: Transparent Liquid Composition

| (1) 7-Chloro-3-methyl-2H-[benzo-1,2,4-thiadiazine]-1,1-dioxide | 1.0% |
|---|---|
| (2) BA | 7.0 |
| (3) DMSO | 5.0 |
| (4) IPA | 50.0 |
| (5) Polyethylene glycol 200 | 5.0 |
| (6) 2-Lauryl-1-hydroxyethyl-1-carboxymethyl imidazolium betaine | 1.4 |
| (7) Lauryl dimethylamine oxide | 0.9 |
| (8) Lauric diethanolamide | 0.6 |
| (9) Potassium hydroxide | q.s. |
| (10) Purified water | balance |

Preparation method

A transparent liquid composition was prepared according to the method of Example 29. The pH of the composition was adjusted to about 9.3.

Example 33: Transparent Liquid Composition

| (1) 7-Chloro-3-methyl-2H-[benzo-1,2,4-thiadiazine]-1,1-dioxide | 5.0% |
|---|---|
| (2) BA | 15.0 |
| (3) IPA | 50.0 |
| (4) Aqueous sodium lactate solution (50%) | 8.0 |
| (5) N,N-Dimethyl-N-lauryl-N-carboxymethyl ammonium betaine | 2.0 |
| (6) 2-Lauryl-1-hydroxyethyl-1-carboxymethyl imidazolinium betaine | 0.7 |
| (7) Lauryl dimethylamine oxide | 0.9 |
| (8) Lauric diethanol amide | 0.9 |
| (9) Sodium hydroxide | q.s. |
| (10) Purified water | balance |

Preparation method

A transparent liquid composition was prepared according to the method of Example 29. The pH of the composition was adjusted to about 10.6.

Example 34: Transparent Liquid Composition

| (1) 7-Chloro-3-methyl-2H-[benzo-1,2,4-thiadiazine]-1,1-dioxide | 4.0% |
|---|---|
| (2) DMSO | 15.0 |
| (3) IPA | 45.0 |
| (4) N,N-dimethyl-N-lauryl-N-carboxylmethyl ammonium betaine | 1.4 |
| (5) Polyoxyethylene (10 mole) oleylamine | 0.8 |
| (6) Lauric diethanolamide | 0.75 |
| (7) Sodium hydroxide | q.s. |
| (8) Purified water | balance |

Preparation method

A transparent liquid composition was prepared according to Example 29. The pH of the composition was adjusted to about 10.6.

Example 35: Hair Tonic

| (1) 7-Chloro-3-methyl-2H-[benzo-1,2,4-thiadiazine]-1,1-dioxide | 0.03% |
|---|---|
| (2) Hinokitiol | 0.01 |
| (3) Retinol palmitate | 0.1 |
| (4) Vitamin E acetate | 0.05 |
| (5) Vitamin B$_6$ | 0.1 |
| (6) BA | 10.0 |
| (7) IPA | 25.0 |
| (8) Ethyl alcohol | 35.0 |
| (9) Propylene glycol | 5.0 |
| (10) Perfume | q.s. |
| (11) 1-Lauryl-1-hydroxyethyl-1-carboxymethyl imidazolynium betaine | 0.7 |
| (12) Polyoxyethylene (10 mole) oleylamine | 0.8 |
| (13) Polyoxyethylene (15 mole) oleyl alcohol | 4.0 |
| (14) Sodium hydroxide | q.s. |
| (15) Purified water | balance |

Preparation method

After (14) was dissolved in (15), (1) was added thereto; followed by heating to 50° C. (6), (7), (9), (11), and (12) were then added, while stirring, to dissolve (1) in the mixture. Thus, a transparent liquid composition (A) was prepared.

On the other hand, (2), (3), (4), (5), (10), and (13) were successively added and dissolved in (8), and thus the composition (B) was prepared. To the composition (A), the composition (B) was added, while stirring. The mixture was then stirred and mixed, followed by filtration, and thus a transparent liquid hair tonic was prepared.

Example 36: Gel Type Hair Growth Preparation

| (1) 7-Chloro-3-methyl-2H-[benzo-1,2,4-thiadiazine]-1,1-dioxide | 2.0% |
|---|---|
| (2) Hirokitiol | 0.01 |
| (3) Pantothenyl ethyl ether | 0.05 |
| (4) BA | 10.0 |
| (5) IPA | 40.0 |
| (6) Dipropylene glycol | 10.0 |
| (7) Glycerol | 5.0 |
| (8) Hydroxypropyl cellulose | 1.0 |
| (9) Carboxyvinyl polymer | 1.0 |
| (10) N,N-Dimethyl-N-lauryl-N-carboxymethyl ammonium betaine | 0.3 |
| (11) Lauric diethanolamide | 2.75 |
| (12) Polyoxyethylene hydrogenated castor oil (P.O.E. = 60 mole) | 2.0 |
| (13) Sodium hydroxide | q.s. |
| (14) Purified water | balance |

Preparation method

After (13) was dissolved in a portion of (14), (1) was added thereto, followed by heating to 50° C., and thus (1) was thoroughly dispersed. To this mixture, (6), (7), a portion of (5), (4), (10) and (11) were successively added, followed by stirring, and thus (1) was completely dissolved to obtain the transparent liquid composition (A).

On the other hand, (2), (3), and (12) were dissolved in the remainder of (5), followed by dispersing (8) therein. Thus, the composition (B) was prepared.

Furthermore, (9) was dispersed and dissolved in the remainder of (14) to prepare the composition (C).

While stirring, the composition (C) was added to the composition (B), followed by thoroughly mixing. The composition (A) was gradually added to this mixture, and thus a transparent gel-like composition was obtained.

Example 37: Emulsion

| | | |
|---|---|---|
| (1) | 7-Chloro-3-methyl-2H-[benzo-1,2,4-thiadiazine]-1,1-dioxide | 0.05% |
| (2) | BA | 5.0 |
| (3) | IPA | 20.0 |
| (4) | Dipropylene glycol | 15.0 |
| (5) | Liquid paraffin | 3.0 |
| (6) | Cetyl alcohol | 0.2 |
| (7) | Lauryl dimethylamine oxide | 1.2 |
| (8) | Polyoxyethylene (15 mole) oleyl amine | 3.5 |
| (9) | Carboxyvinyl polymer | 0.2 |
| (10) | Perfume | q.s. |
| (11) | Polyoxyethylene hydrogenated castor oil (P.O.E. = 40 mol) | 1.0 |
| (12) | Preservative | q.s. |
| (13) | Sodium hexamethaphosphate | 0.03 |
| (14) | Potassium hydroxide | q.s. |
| (15) | Purified water | balance |

Preparation method

After (14) was dissolved in a portion of (15), (1) was added thereto, followed by heating to 50° C., and thereafter, a portion of (4), (3), and (2) were added thereto, whereby (1) was dissolved. Furthermore, (7) and (8) were added and the mixture was dissolved to prepare the composition (A).

To the remainder of (4), a portion of (15) and (11) were added and the mixture was dissolved upon heating to 50° C. While the mixture was stirred in a monomixer, the mixture obtained by adding (6), (10), and (12) to (5), followed by mixing at 70° C. was gradually added, and thus the emulsified composition (B) was obtained.

After (9) and (13) were dissolved in the remainder of (15), the compositions (B) and (A) obtained above were successively added thereto while stirring, followed by mixing under stirring in a homomixer. After cooling, an emulsion was obtained.

Example 28: Cream

| | | |
|---|---|---|
| (1) | 7-Chloro-3-methyl-2H-[benzo-1,2,4-thiadiazine]-1,1-dioxide | 0.1% |
| (2) | Vitamin E acetate | 0.05 |
| (3) | BA | 5.0 |
| (4) | IPA | 25.0 |
| (5) | Polyethylene glycol 200 | 13.0 |
| (6) | Glycerol | 4.0 |
| (7) | Liquid paraffin | 1.0 |
| (8) | Castor oil | 3.5 |
| (9) | Perfume | q.s. |
| (10) | N,N-Dimethyl-N-lauryl-N-carboxymethyl ammonium betaine | 1.2 |
| (11) | Lauric diethanol amide | 1.8 |
| (12) | Glycerol monofatty acid ester | 1.5 |
| (13) | Preservative | q.s. |
| (14) | Clay mineral (bentonite) | 6.0 |
| (15) | Potassium hydroxide | q.s. |
| (16) | Purified water | balance |

Preparation method

After (15) was added and dissolved in a portion of (16), (1) was added and the mixture was heated to 50° C. Then, (3), (4), (5), and (6) were added to dissolve (1), and (10) and (11) were then added, followed by dissolving while stirring. Thus, the composition (A) was prepared.

To (7) were successively added (2), (8), (9), (12), and (13), the mixture was heated to 70° C. and mixed to prepare a solution, and thus the composition (B) was prepared.

At a temperature maintained at 70° C., while stirring the composition (A), the composition (B) was gradually added to effect preliminary emulsification, followed by emulsification by a homomixer.

This emulsion was added to a dispersion previously prepared by adding (14) to the remainder of (16) under stirring, and the mixture then cooled to obtain a cream.

| Stock solution recipe | | |
|---|---|---|
| (1) | 7-Chloro-3-methyl-2H-[benzo-1,2,4-thiadiazine]-1,1-dioxide | 0.6% |
| (2) | Ethynyl estradiol | 0.001 |
| (3) | Pantothenyl ethyl ether | 0.05 |
| (4) | BA | 6.0 |
| (5) | IPA | 37.0 |
| (6) | Ethyl alcohol | 37.0 |
| (7) | Dipropylene glycol | 15.0 |
| (8) | 2-Lauryl-1-hydroxyethyl-1-carboxymethyl imidazolium betaine | 0.34 |
| (9) | Polyoxyethylene (10 mol) oleyl amine | 6.4 |
| (10) | Polyoxyethylene hydrogenated castor oil (P.O.E.: 60 mole) | 1.0 |
| (11) | Perfume | q.s. |
| (12) | Sodium hydroxide | q.s. |
| (13) | Purified water | balance |
| Filling recipe | | |
| (14) | Stock solution | 30.0% |
| (15) | Freon 12 | 42.0 |
| (16) | Freon 13 | 28.0 |

Preparation method

A stock solution was prepared according to the method of Example 35.

Filling was carried out by filling the stock solution (13) at a prescribed amount into a can and, after mounting a valve, the gases (14) and (15) were successively filled in prescribed amounts.

We claim:

1. A dissolved composition comprising:
   (A) at least one [benzo-1,2,4-thiadiazine]-1,1-dioxide;
   (B) dimethyl sulfoxide, benzyl alcohol, or the mixture thereof;
   (C) water; and
   (D-2) at least one surfactant, other than anionic surfactants, having a nitrogen atom in the molecule thereof.

2. A dissolved composition according to claim 1, further comprising (D-1) at least one anionic surfactant.

3. A dissolved composition as claimed in claim 1, wherein said component (D-2) includes at least one amine oxide.

4. A dissolved composition as claimed in claim 2, wherein said component (D-2) includes at least one amine oxide.

5. A dissolved composition as claimed in claim 1 containing 0.005% to 10% by weight of the component (A), 1.0% to 30% by weight of the component (B), 1.0% to 70% by weight of the component (C), and 0.001% to 10% by weight of the component (D), based on the total weight of the composition.

6. A dissolved composition as claimed in claim 1 further comprising (E) isopropyl alcohol.

7. A dissolved composition as claimed in claim 5 further comprising 10% to 85% by weight of (E) isopropyl alcohol.

8. A dissolved composition as claimed in claim 1 further comprising (F) a pH controller for controlling the pH of the composition to the range of 8.5 to 11.0.

9. A hair germination and hair growth promoting agent containing as an effective ingredient a dissolved composition as claimed in claim 1.

10. A dissolved composition as claimed in claim 2, wherein the [benzo-1,2,4-thiadiazine]-1,1-dioxide has the formula:

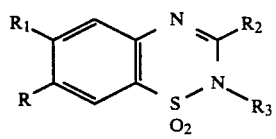

wherein R is Cl, $CF_3$, $SO_2$, or $NH_2$, $R_1$ is H, Cl, $SO_2$, or $NH_2$, $R_2$ is H, $C_nH_{2n+1}$ wherein n is an integer of 1 to 10, $CH_2OH$, $COOH$, or $CH_2C_6H_5$, $R_3$ is H, $C_mH_{2m+1}$ wherein m is an integer of 1 to 10 or $CH_2C_6H_5$.

11. A dissolved composition as claimed in claim 2 containing 0.005% to 10% by weight of the component (A), 1.0% to 30% by weight of the component (B), 1.0% to 70% by weight of the component (C), and 0.001% to 10% by weight of the components (D-1) and (D-2), based on the total weight of the composition, the molar ratio of said components (D-1):(D-2) being 20:1 to 1:20.

12. A dissolved composition as claimed in claim 2 further comprising (E) isopropyl alcohol.

13. A dissolved composition as claimed in claim 11 further comprising 10% to 85% by weight of (E) isopropyl alcohol.

14. A dissolved composition as claimed in claim 2 further comprising (F) a pH controller for controlling the pH of the composition to the range of 8.5 to 11.0.

15. A hair germination and hair growth promoting agent containing as an effective ingredient a dissolved composition as claimed in claim 2.

16. A dissolved composition comprising:
(A) at least one [benzo-1,2,4-thiadiazine]-1,1-dioxide;
(B) dimethyl sulfoxide, benzyl alcohol, or the mixture thereof;
(C) water; and
(D″) (i) at least one surfactant selected from the group consisting of ampholytic surfactants and one surfactant selected from the group consisting of nonionic surfactants having a nitrogen atom in the molecule thereof.

17. A dissolved composition as claimed in claim 16, wherein the [benzo-1,2,4-thiadiazine]-1,1-dioxide has the formula:

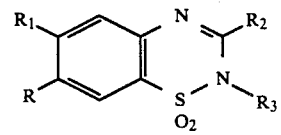

wherein R is Cl, $CF_3$, $SO_2$, or $NH_2$, $R_1$ is H, Cl, $SO_2$, or $NH_2$, $R_2$ is H, $C_nH_{2n+1}$ wherein n is an integer of 1 to 10, $CH_2OH$, $COOH$, or $CH_2C_6H_5$, $R_3$ is H, $C_mH_{2m+1}$ wherein m is an integer of 1 to 10 or $CH_2C_6H_5$.

18. A dissolved composition as claimed in claim 16 containing 0.005% to 10% by weight of the component (A), 1.0% to 30% by weight of the component (B), 1.0% to 70% by weight of the component (C), and 0.001% to 10% by weight of the component (D″), based on the total weight of the composition.

19. A dissolved composition as claimed in claim 16 further comprising (E) isopropyl alcohol.

20. A dissolved composition as claimed in claim 18 further comprising 10% to 85% by weight of (E) isopropyl alcohol.

21. A dissolved composition as claimed in claim 16 further comprising (F) a pH controller for controlling the pH of the composition to the range of 8.5 to 11.0.

22. A hair germination and hair growth promoting agent containing as an effective ingredient a dissolved composition as claimed in claim 16.

23. In the method of application of (A) a [benzo-1,2,4-thiadiazine]-1,1-dioxide to an individual to promote hair growth on said individual, the improvement wherein said dioxide is topically applied dissolved in a solvent comprising (B) dimethyl sulfoxide, benzyl alcohol, or the mixture thereof; (C) water; and (D) at least one surfactant selected from the group consisting of anionic surfactants and surfactants, other than anionic surfactants, having a nitrogen atom in the molecule thereof.

24. The method according to claim 23, wherein (D) comprises (i) at least one surfactant selected from the group consisting of ampholytic surfactants and nonionic-cationic-polar surfactants and (ii) at least one surfactant selected from the group consisting of nonionic surfactants having a nitrogen atom in the molecule thereof.

25. In the method of application (A) [benzo-1,2,4-thiadiazine]-1,1-dioxide to an individual to promote hair growth on said individual, the improvement wherein said dioxide is topically applied dissolved in a solvent comprising (B) dimethyl sulfoxide, benzyl alcohol, or the mixture thereof; (C) water; and (D-2) at least one surfactant, other than anionic surfactants, having a nitrogen atom in the molecule thereof.

26. The method as claimed in claim 25, wherein said component (D-2) includes at least one amino oxide.

* * * * *

UNITED STATES PATENT AND TRADEMARK OFFICE
CERTIFICATE OF CORRECTION

PATENT NO. : 4,985,425

DATED : January 15, 1991

INVENTOR(S) : Chiba et al.

It is certified that error appears in the above-identified patent and that said Letters Patent is hereby corrected as shown below:

Col. 25, line 48    After " and " insert -- nonionic cationic-polar surfactants and (ii) at least --

Signed and Sealed this

Twentieth Day of October, 1992

Attest:

DOUGLAS B. COMER

Attesting Officer    Acting Commissioner of Patents and Trademarks